(12) United States Patent
Dorsey

(10) Patent No.: US 10,751,716 B1
(45) Date of Patent: Aug. 25, 2020

(54) LATERAL MEDIA FLOW MICROTITER PLATE

(71) Applicant: U.S. Army Edgewood Chemical Biological Center, APG, MD (US)

(72) Inventor: Russell M. Dorsey, Fallston, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 370 days.

(21) Appl. No.: 15/934,395

(22) Filed: Mar. 23, 2018

(51) Int. Cl.
*B01L 3/00* (2006.01)

(52) U.S. Cl.
CPC ......... *B01L 3/50273* (2013.01); *B01L 3/5027* (2013.01); *B01L 2200/141* (2013.01); *B01L 2300/087* (2013.01); *B01L 2300/0877* (2013.01); *B01L 2300/0893* (2013.01)

(58) Field of Classification Search
None
See application file for complete search history.

(56) References Cited

FOREIGN PATENT DOCUMENTS

WO    WO-2016166315 A1 * 10/2016 ............ C12M 23/38

* cited by examiner

*Primary Examiner* — Paul S Hyun
(74) *Attorney, Agent, or Firm* — Ulysses John Biffoni

(57) ABSTRACT

A microtiter plate for flow of fluid across a plurality of wells is provided, including a base; a plurality of wells disposed on the base in a plurality of rows, wherein each well is fluidly coupled to each adjacent well within a row of wells; an inlet fluidly coupled to a first well in a row of wells; and an outlet fluidly coupled to a last well in a row of wells; wherein the microtiter plate is configured such that fluid injected through the inlet flows from the first well to the last well and is ejected through the outlet. Systems it microtiter plates and a pump and/or exhaust tube are also provided.

17 Claims, 3 Drawing Sheets

LATERAL MEDIA FLOW MICROTITER PLATE

GOVERNMENT INTEREST

The invention described herein may be manufactured, used, and licensed by or for the United States Government.

FIELD

The present disclosure relates to microtiter plates. More specifically, provided herein are microtiter plates that enable unilateral flow of fluid, including tissue culture media, across a series of adjacent wells.

BACKGROUND

Currently, animal models serve as gold standards for testing of drug efficacy or the effects of toxicants on the body. However, studies have shown that rodent and non-rodent animal species are predictive for human toxicity only 43% and 63%, respectively. Additional drawbacks associated with such models are high costs and low throughput. Given the drawbacks to animal use, efforts are ongoing to transition to in vitro tests. One serious drawback to in vitro tests is that they are restricted to a single cell/tissue type (liver, heart, lung, etc.) per well of microtiter plate; this prevents the evaluation of multi-organ effects. To overcome this limitation, chips containing cells or tissue have been linked through microfluidics. These systems have the key feature of utilizing pumps to drive the flow of tissue culture media over tissue cells unilaterally, thus simulating blood flow from one organ to the next as occurs in vivo. However, these systems are prone to contamination and are not compatible with standard laboratory analysis equipment such as microplate readers or microscopes. A need exists for improved model systems to assess drug efficacy and toxicant effects on the body.

SUMMARY

The following summary is provided to facilitate an understanding of some of the innovative features unique to the present disclosure and is not intended to be a full description. A full appreciation of the various aspects of the disclosure can be gained by taking the entire specification, claims, drawings, and abstract as a whole.

In one aspect, a microtiter plate for unilateral flow of fluid across a plurality of wells is provided, comprising: a base; a plurality of wells disposed on the base in a plurality of rows, wherein each well is fluidly coupled to each adjacent well within a row of wells; an inlet fluidly coupled to a first well in a row of wells; and an outlet fluidly coupled to a last well in a row of wells; wherein the microtiter plate is configured such that fluid injected through the inlet flows from the first well to the last well and is ejected through the outlet.

In another aspect, a system for unilateral flow of tissue culture media across a plurality of wells in a microtiter plate is provided, comprising: a microliter plate comprising a base; a plurality of wells disposed on the base in a plurality of rows, wherein each well is fluidly coupled to each adjacent well within a row of wells; an inlet fluidly coupled to a first well in a row of wells; and an outlet fluidly coupled to a last well in a row of wells; and a pump fluidly coupled to the inlet for pumping tissue culture media across a plurality of wells; wherein the system is configured such that tissue culture media pumped through the inlet flows from the first well to the last well and is ejected through the outlet.

BRIEF DESCRIPTION OF THE DRAWINGS

The aspects set forth in the drawings are illustrative and exemplary in nature and not intended to limit the subject matter defined by the claims. The following detailed description of the illustrative aspects can be understood when read in conjunction with the following drawings, where like structure is indicated with like reference numerals and in which:

DETAILED DESCRIPTION

Figure 1:
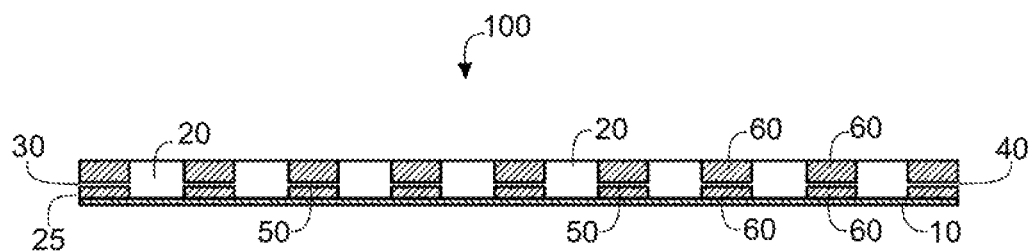
FIG. 1 depicts a cross-section view of a row of wells on a microtiter plate, the row comprising an inlet, and outlet, and channels fluidly coupling adjacent wells within the row.

The following description of particular aspect(s) is merely exemplary in nature and is in no way intended to limit the scope of the disclosure, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes or compositions are described as an order of individual steps or using specific materials, it is appreciated that steps or materials may be interchangeable such that the description of the invention may include multiple parts or steps arranged in many ways as is readily appreciated by one of skill in the art.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third" etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, "a first element," "component," "region," "layer," or "section" discussed below could be termed a second (or other) element, component, region, layer, or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "and combinations thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Scientific and technical terms used herein are intended to have the meanings commonly understood by those of ordinary skill in the art. Such terms are found defined and used in context in various standard references illustratively including J. Sambrook and D. W., Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W. H. Freeman & Company, 2004; Wild, D., The Immunoassay Handbook, 3rd Ed., Elsevier Science, 2005; Gosling, J. P., Immunoassays: A Practical Approach, Practical Approach Series, Oxford University Press, 2005; Antibody Engineering, Kontermann, R. and Dübel, S. (Eds.), Springer, 2001; Harlow, E. and Lane, D., Antibodies: A Laboratory Manual, Cold Spring Harbor Laboratory Press, 1988; Ausubel, F. et al., (Eds.), Short Protocols in Molecular Biology, Wiley, 2002; D. Pound (Ed.) Immunochemical Protocols, Methods in Molecular Biology, Humana Press; 2nd ed., 1998: B.K.C. Lo (Ed.), Antibody Engineering: Methods and Protocols, Methods in Molecular Biology, Humana Press, 2003; and Kohler, G. and Milstein, C., Nature, 256:495-497 (1975); the contents of each of which are incorporated herein by reference.

In order to take advantage of both positive aspects of media flow between tissues and the ability to measure endpoints on standard laboratory equipment, disclosed herein are modified microtiter plates wherein adjacent wells are fluidly coupled via open channels which permit lateral flow of fluid across a series of wells. The microtiter plates and systems disclosed herein have utility in assessing drug efficacy and toxicity and in simulating first pass metabolism of drugs in vivo.

Various aspects of the present disclosure are illustrated by the following non-limiting examples. The examples are for illustrative purposes, and are not a limitation on any, practice of the presently disclosed aspects. It will be understood that variations and modifications can be made without departing from the spirit and scope of the disclosure.

Figure 2:
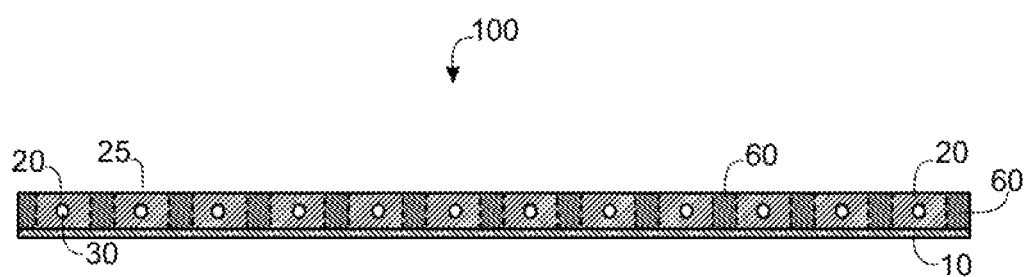
FIG. 2 depicts an end view of a microtiter plate having a series of inlets for injecting fluid across a plurality of rows of wells.

FIGS. 1 and 2 depict a microtiter plate 100 for unilateral flow of fluid across a plurality of wells. FIG. 1 depicts a cross-section view of a microtiter plate 100 comprising: a base 10; a plurality of wells 20 disposed on the base 10 in a row 25, wherein each well 20 is fluidly coupled to each adjacent well 20 within the row 25 of wells; an inlet 30 fluidly coupled to a first well 20 in the row 25; and an outlet 40 fluidly coupled to a last well 20 in the row 25; wherein the microtiter plate 100 is configured such that fluid injected through the inlet 30 flows from the first well in the row across intervening wells to the last well in the row and is ejected through the outlet 40.

Adjacent wells 20 are optionally coupled via an open channel 50 fluidly coupling the wells. By "open," it is understood that the channel does not comprise a membrane, film, filter, or the like, which would serve as a barrier or partial barer to the exchange of fluid between adjacent wells 20. Optionally, a channel is not an open channel and optionally includes a membrane or other filtration apparatus or section that partially or selectively allows transfer of fluid material from one well to an adjacent well. In certain aspects, the channel 50 traverses an interstitial area 60 between adjacent wells 20 on a microtiter plate 100. Each channel 50 permits the lateral flow of fluid from one well 20 to an adjacent well 20, while prohibiting leakage of said fluid into the interstitial area 60 between the wells.

Dimensions of the channels 50 may vary, depending on the number of wells and configuration thereof. The diameter of the channels can range, for example, from 500 micrometers (μm) to 6 millimeters (mm), optionally 1 mm to 6 mm, optionally 2 mm to 6 mm, optionally 3 mm to 6 mm, optionally 3 mm to 5 mm.

The interstitial are 60 between wells is optionally at least partially filled with a solid material. In some aspects, adjacent wells 20 may be fluidly coupled via a notch at a top surface of each well (not shown), wherein a channel is disposed between notches to fluidly couple adjacent wells. In other aspects, a channel 50 is bored through the walls of adjacent wells in the plate, optionally traversing solid interstitial area 60 as well as a row 25 of wells 20 to enable fluid communication between adjacent wells 20 within the row 25. Optionally, the microtiter plate 100 is molded or printed, for example, via injection molding or 3D-printing. Systems and methods for molding or printing are known in the art and within the purview of the skilled artisan.

In one aspect, the microtiter plate disclosed herein is a 96-well microtiter plate, comprising wells arranged in a 2:3 rectangular matrix (i.e., either eight rows of twelve wells, or twelve rows of eight wells, depending on orientation of the plate). It is understood that various configurations of microtiter plates are standard and may be utilized in the devices described herein. For example, a microtiter plate according to this disclosure may contain 96, 384, 1536, or more wells arranged in a 2:3 rectangular or other matrix arrangement. Microtiter plates disclosed herein may be manufactured from a variety of materials, including but not limited to polystyrene, polypropylene, polycarbonate, cyclo-olefins, and any other suitable material. In particular aspects, the microtiter plate is a polystyrene plate suitable for use in tissue culture applications and assays.

In certain aspects, a microtiter plate according to the present disclosure is manufactured by modifying a standard microtiter plate. Interstitial area between wells on the plate is at least partially filled with a solid material, such as a resin or other suitable filler. A conduit is then bored through the plate to form open channels that traverse solid interstitial area between wells, thereby fluidly coupling a series of wells within a row and simultaneously forming an inlet and outlet for the row. The conduit is fluid-tight and prohibits leakage of fluid into the solid interstitial area between wells.

FIG. 2 depicts an end view of a 96-well microtiter plate 100. In this aspect, the microtiter plate 100 comprises twelve rows 25 of wells 20, each row 25 having an inlet 30 fluidly coupled to the first well in the row, through which fluid is injected into the microtiter plate 100. An outlet 40 (not shown) is fluidly coupled to the last well in each row 25, such that fluid injected through the inlet 30 flows unilaterally across all wells in the row 25 and is ejected through the last well 20 via outlet 40. It will be appreciated that plates having various configurations of wells can be utilized in the devices disclosed herein.

Figure 3:
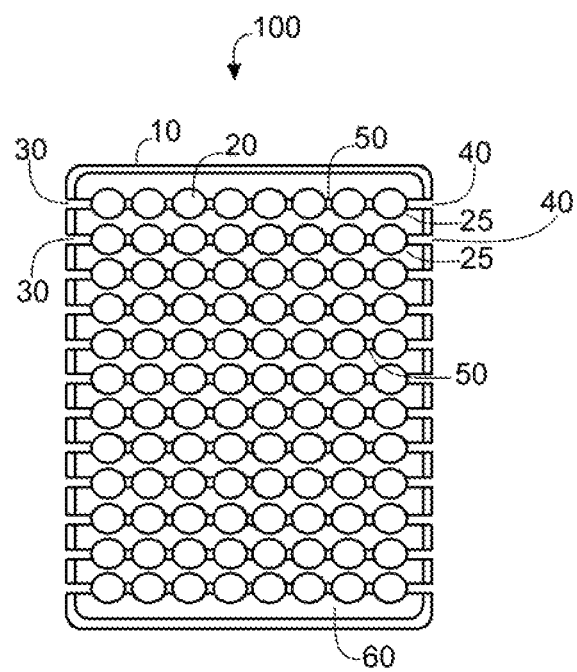
FIG. 3 depicts a top view of a microtiter plate, wherein each row of wells comprises an inlet and an outlet and adjacent wells within each row are fluidly coupled via channels.

The skilled artisan will appreciate that adjacent wells and/or rows can be coupled in a variety of configurations. FIG. 3 depicts a top view of an exemplary aspect of a microliter plate 100, wherein each row 25 of wells 20 comprises an inlet 30 and an outlet 40, such that all wells 20 within in a single row 25 are fluidly coupled in series via channels 50. In this aspect, fluid injected through the inlet 30 traverses all wells 20 within a row 25 in series and is ejected through the outlet 40.

Figure 4:
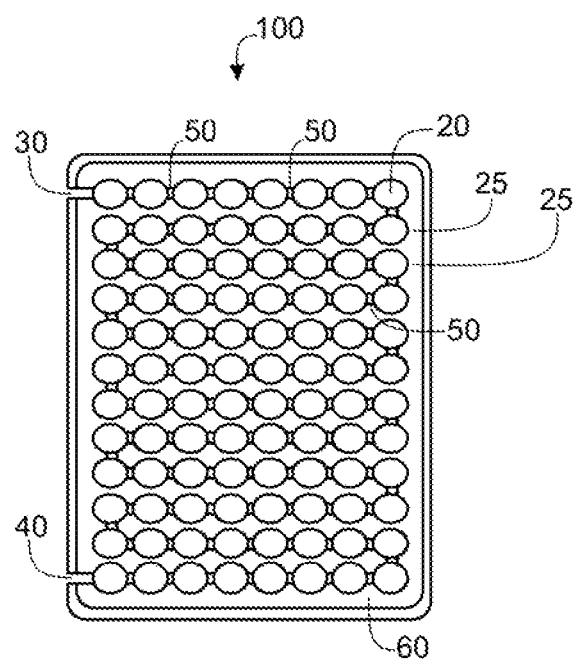
FIG. 4 depicts a top view of a microliter plate comprising one inlet and one outlet, wherein adjacent wells within a row are fluidly coupled, and wherein adjacent rows are fluidly coupled at one end to provide continuous lateral fluid allow from a first well to a last well on the plate.

Optionally, one or more rows of wells may also be fluidly coupled. For example, 2 3, 4, or more rows including all rows of wells on a microtiter plate can also be fluidly coupled as desired. A variety of configurations a suitable for such aspects. FIG. 4 depicts a top view of an aspect of microtiter plate 100 wherein each well 20 is fluidly coupled to each adjacent well 20 within each row 25, and wherein each row 25 is fluidly coupled to each adjacent row 25 at an end well 20. In such an aspect, the microtiter plate comprises only one inlet 30 and one outlet 40, such that fluid injected through the inlet 30 traverses each well 20 of the microtiter plate 100 in series, passing through the channels 50, and is ejected via one outlet 40. The microtiter plate can be manufactured such that any number of rows are fluidly coupled in series. For example, in certain aspects, two adjacent rows of fluidly coupled wells may be fluidly coupled at an end well, such that fluid injected through an inlet in the first row traverses each rows of wells and is ejected through an outlet in the second row (not pictured). Other configurations of fluidly coupled rows are within the purview of the skilled artisan.

Also provided herein is a system for unilateral flow of fluid, such as tissue culture or other desired media, across a plurality of wells in a microtiter plate, comprising: a microtiter plate comprising a base; a plurality of wells disposed on the base in a plurality of rows, wherein each well is fluidly coupled to each adjacent well within a row of wells; an inlet fluidly coupled to a first well in a row of wells; and an outlet fluidly coupled to a last well in a row of wells; and a pump fluidly coupled to the inlet for pumping tissue culture media across a plurality of wells; wherein the system is configured such that tissue culture media pumped through the inlet flows from the first well to the last well and is ejected through the outlet.

In certain aspects, adjacent wells are fluidly coupled via a channel that traverses an interstitial area between wells. As described above, in some aspects of a system as described herein, the interstitial area is at least partially filed with a solid material. Connecting channels traverse the solid interstitial area to connect adjacent wells in a row. The microtiter plates of the systems according to the present disclosure can comprise various configurations of fluidly coupled wells, including but not limited to configurations wherein each well within a row is fluidly coupled, or wherein two or more adjacent rows are further fluidly coupled.

In certain aspects, the microtiter plates and systems disclosed herein comprise one or more fittings for connecting a pump and/or exhaust tube to the microtiter plate.

Figure 5A:
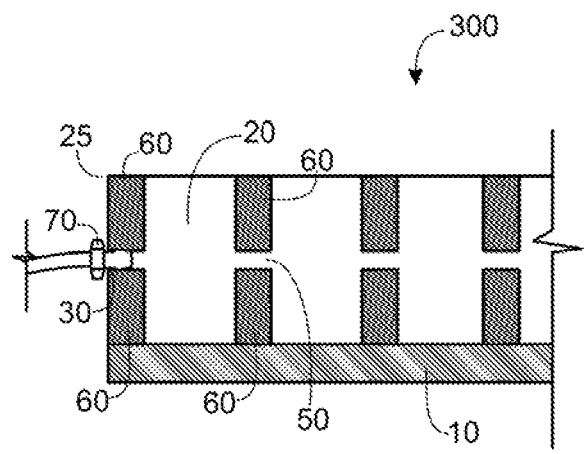
FIG. 5A depicts a cross-section view of a row of wells on a microtiter plate, wherein a first well comprises an inlet having a bathed-tube fitting for coupling a pump to the microtiter plate.
Figure 5B:
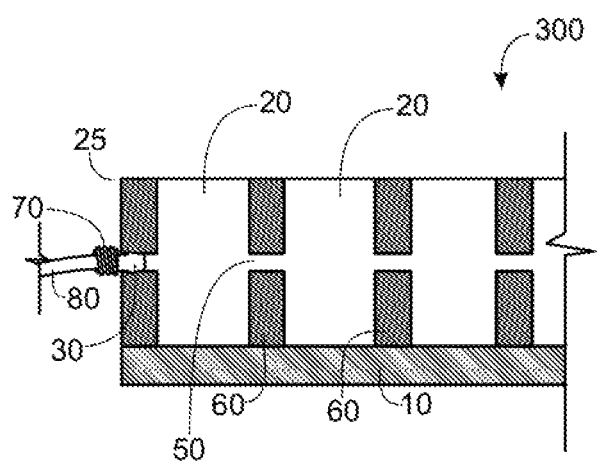
FIG. 5B depicts a cross-section view of a row of wells on a microliter plate, wherein a first well comprises an inlet having a threaded or bier fitting for coupling a pump to the microtiter plate.

FIGS. 5A and 5B depict cross-section views of a portion of a system 300, wherein the inlet 30 is connected to a fitting 70. The fitting 70 facilitates connection between the inlet 30 and a pump (not shown) for pumping fluid, particularly tissue culture media, across a row 25 of wells 20. A tube 80 connects a pump to the fitting 70. While a fitting is not required for the microtiter plate to function and a pump can optionally be connected directly to the inlet 30 without a fitting, in certain aspects a fitting is desirable to assist in connecting the pump to the microtiter plate. FIG. 5A depicts a barbed tube fitting 70, and FIG. 5B depicts a threaded luer fitting 70. While these fittings 70 are depicted as being connected to the inlet 30, it is appreciated that the outlet can also optionally be connected to a fitting. In such aspects, the outlet is connected to a fitting, which may be connected to an exhaust tube (not shown). Various types of fittings are suitable for use in the disclosed microtiter plates, including but not limited to barbed tube fittings, threaded luer fittings, taper joint tube adaptors, and the like. A plurality of fittings 70 on a microtiter plate need not be identical and can include a combination of fitting types.

A variety of pumps suitable for pumping fluid, including tissue culture media, across a plurality of wells are known in the art. Suitable pumps for use with the presently disclosed microtiter plates and systems include, but are not limited to, peristaltic pumps and syringes. Unilateral, defined flow of fluid is thus dependent on pump speed. Generally, the microtiter plates disclosed herein have loose-fitting lids, such that the plates and systems, disclosed herein are not pressurized. Unilateral flow of tissue culture media can therefore simulate in vivo single pass metabolism across a variety of cell types.

Various modifications of the present disclosure, in addition to those shown and described herein, will be apparent to those skilled in the art of the above description. Such modifications are also intended to fall within the scope of fire appended claims.

It is appreciated that all reagents are obtainable by sources known in the art unless otherwise specified. Methods of tissue culture and assays for assessing drug efficacy and toxicity are similarly within the level of skill in the art.

Patents, publications, and applications mentioned in the specification are indicative of the levels of those skilled in the art to which the disclosure pertains. These patents, publications, and applications are incorporated herein by reference to the same extent as if each individual patent, publication, or application was specifically and individually incorporated herein by reference.

The foregoing description is illustrative of particular aspects of the disclosure, but is not meant to be a limitation upon the practice thereof. The following claims, including all equivalents thereof, are intended to define the scope of the disclosure.

The invention claimed is:

1. A microtiter plate for unilateral flow of fluid across a plurality of wells, comprising:
   a base;
   a plurality of wells disposed on the base in a plurality of rows, wherein each well in a row is fluidly coupled to each adjacent well within said row;

an inlet fluidly coupled to a first well in a first row of wells;
an outlet fluidly coupled to a last well in said first row of wells; and
a fitting connected to the inlet for fluidly coupling a pump to the microtiter plate, wherein the fitting is selected from the group consisting of a barbed tube fitting, a threaded luer fitting, and a taper joint tube adapter;
wherein the microtiter plate is configured such that fluid injected through the inlet flows from the first well to the last well and is transmitted through the outlet.

2. The microtiter plate according to claim 1, wherein adjacent wells in each row are fluidly coupled via a channel that traverses an interstitial area between the adjacent wells.

3. The microtiter plate according to claim 2, wherein the channel is enclosed within the interstitial area between the adjacent wells.

4. The microtiter plate according to claim 2, wherein the interstitial area between the adjacent wells of the microtiter plate is at least partially filled with a solid material.

5. The microtiter plate according to claim 1, wherein each row of said plurality of rows includes an inlet fluidly coupled to a first well in each of said plurality of rows and an outlet fluidly coupled to a last well in each of said plurality of rows, so that fluid injected through the inlet fluidly coupled to the first well of a row traverses all wells within said row in series and is ejected out of the microtiter plate through the outlet fluidly coupled to the last well of said row.

6. The microtiter plate according to claim 5, further comprising a fitting connected to the outlet fluidly coupled to the last well of a row for fluidly coupling an exhaust tube to the microtiter plate.

7. The microtiter plate according to claim 6, wherein the fitting connected to the outlet is selected from the group consisting of a barbed tube fitting, a threaded luer fitting, and a taper joint tube adapter.

8. The microtiter plate according to claim 5, further comprising:
a pump fluidly coupled to the inlet fluidly coupled to the first well of a row, for pumping media through each well in the row and out of the microtiter plate through the outlet fluidly coupled to the last well of the row.

9. The microtiter plate according to claim 8, wherein the fitting comprises a first fitting connected to the inlet fluidly coupled to the first well in the first row of wells for fluidly coupling the pump to the microtiter plate, and further comprising a second fitting connected to the outlet fluidly coupled to a last well of a row for coupling an exhaust tube, wherein the second fitting is independently selected from the group consisting of a barbed tube fitting, a threaded luer fitting, and a taper joint tube adapter.

10. The microtiter plate according to claim 8, wherein the pump is selected from the group consisting of a peristaltic pump and a syringe style pump.

11. The microtiter plate according to claim 1, wherein each row of wells is fluidly coupled to at least one adjacent row of wells.

12. The microtiter plate according to claim 1, wherein a last well in each row is fluidly coupled to a well in an adjacent row, so that fluid injected through the inlet fluidly coupled to the first well in the first row of wells traverses each well of the microtiter plate in series and is ejected from the microtiter plate via the outlet, which is fluidly coupled to a last well in a last row.

13. The microtiter plate according to claim 12, further comprising a fitting connected to the outlet fluidly coupled to the last well in the last row for fluidly coupling an exhaust tube to the microtiter plate.

14. The microtiter plate according to claim 13, wherein the fitting connected to the outlet is selected from the group consisting of a barbed tube fitting, a threaded luer fitting, and a taper joint tube adapter.

15. The microtiter plate according to claim 12, further comprising:
a pump fluidly coupled to the inlet fluidly coupled to the first well of the first row of wells, for pumping media through each well of the microtiter plate in series and wherein the media is ejected from the microtiter plate via the outlet fluidly coupled to the last well in the last row.

16. The microtiter plate according to claim 15, wherein the fitting comprises a first fitting connected to the inlet fluidly coupled to the first well of the first row for fluidly coupling the pump to the microtiter plate, and further comprising a second fitting connected to the outlet fluidly coupled to the last well in the last row for coupling an exhaust tube, wherein the second fitting is independently selected from the group consisting of a barbed tube fitting, a threaded luer fitting, and a taper joint tube adapter.

17. The microtiter plate according to claim 15, wherein the pump is selected from the group consisting of a peristaltic pump and a syringe style pump.

* * * * *